United States Patent [19]

Newton

[11] 4,231,372
[45] Nov. 4, 1980

[54] SAFETY MONITORING CIRCUIT FOR ELECTROSURGICAL UNIT

[75] Inventor: David W. Newton, Boulder, Colo.

[73] Assignee: Valleylab, Inc., Boulder, Colo.

[21] Appl. No.: 520,269

[22] Filed: Nov. 4, 1974

[51] Int. Cl.³ .............................................. A61B 17/36
[52] U.S. Cl. .......................... 128/303.14; 128/303.17; 361/42
[58] Field of Search ...................... 128/303.13, 303.14, 128/303.17, 303.18, 2.1 P, 2.06 A, 908; 317/18 A, 18 B, 18 D, 18 R, 31; 361/42

[56] References Cited

U.S. PATENT DOCUMENTS

| 3,513,353 | 5/1970 | Lansch | 317/31 |
| 3,683,923 | 8/1972 | Anderson | 128/303.14 |
| 3,697,808 | 10/1972 | Lee | 317/18 B |
| 3,784,842 | 1/1974 | Kremer | 317/18 A |
| 3,812,858 | 5/1974 | Oringer | 128/303.14 |
| 3,826,263 | 7/1974 | Cage et al. | 128/303.17 |
| 3,828,768 | 8/1974 | Douglas | 128/2.06 A |
| 3,905,373 | 9/1975 | Gonser | 128/303.14 |

FOREIGN PATENT DOCUMENTS

| 1139927 | 11/1962 | Fed. Rep. of Germany | 128/303.13 |
| 1275415 | 10/1961 | France | 128/303.13 |
| 1347865 | 11/1963 | France | 128/303.14 |

Primary Examiner—Lee S. Cohen
Attorney, Agent, or Firm—Gerald J. Ferguson, Jr.; Joseph J. Baker

[57] ABSTRACT

A safety monitoring circuit for use in an electrosurgical unit is disclosed. The circuit is useful to indicate a fault in the return path between an RF source and a patient electrode in contact with a patient to prevent electrical burns to the patient that can occur due to improper patient contact with the patient electrode or a break in the return path. The circuit includes a current sensor connected in series in the return path to the RF source, which sensor provides an output indicative of the sensed current that is coupled through a DC amplifier to a comparator, the comparator providing an output only if a predetermined threshold is exceeded. When a comparator output is provided, a timer is triggered to energize, for a predetermined period of time, an alarm to indicate a sensed fault and/or actuate disabling circuitry to terminate application of electrical energy to the active electrode utilized in electrosurgery for cutting or coagulation.

8 Claims, 2 Drawing Figures

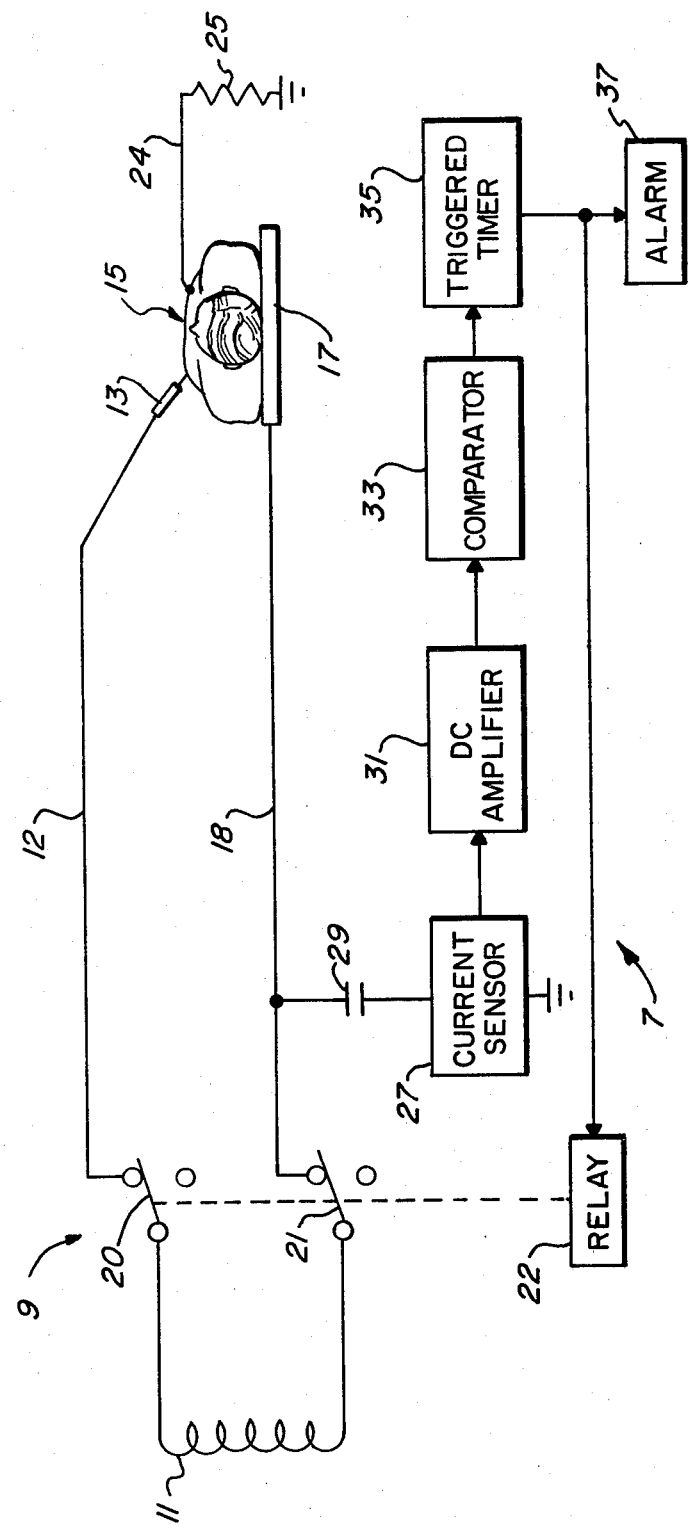

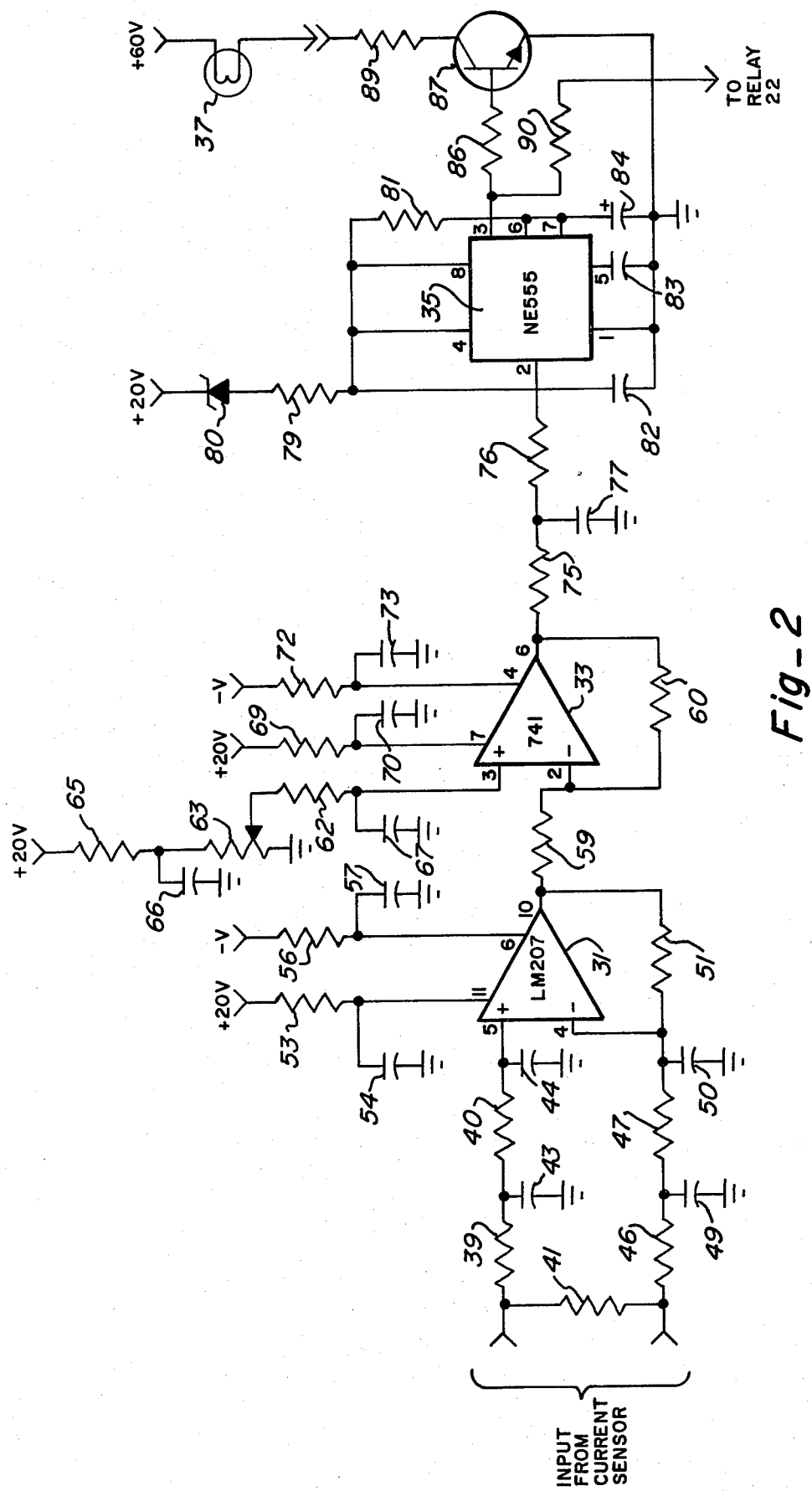

SAFETY MONITORING CIRCUIT FOR ELECTROSURGICAL UNIT

FIELD OF THE INVENTION

This invention relates to a safety monitoring circuit, and, more particularly, relates to a circuit for monitoring the current in the return path of an electrosurgical unit.

BACKGROUND OF THE INVENTION

Electrosurgery has found widespread use in the medical field to perform cutting and coagulating operations. Normally, the patient is placed in contact with a patient electrode or plate connected to the patient terminal of a radio frequency (RF) source. The active terminal of the RF source is then connected to the active electrode of an electrosurgical instrument which is commonly utilized as a cutting or coagulating electrode when brought into patient contact. When so utilized, the RF source applies a high density current to the active electrode at a relatively high voltage and this causes a localized cutting or coagulating action. The current, after flowing through the active electrode, is normally returned through the patient plate to the RF source. To insure a low current density other than at the active electrode, the patient plate is designed to contact the patient over a relatively large area. This results in the needed low current density and thus prevents the occurrence of localized electrical burns as long as the patient plate contacts the patient over the large area.

If the return path connecting the patient plate to the RF source is broken, however, or if the patient should move out of contact with a large area of the patient plate, it has been found that electrical burns can result since there is no longer a low current density connection for return of the RF energy. Such a burn could occur, for example, where there is a secondary return contact to the patient since current can flow through the secondary return contact and thus cause localized burning of the patient at the point where the secondary return contacts the patient.

Such secondary return contacts could exist, for example, where monitoring electrodes are connected to the patient, where there is grounded adjacent metallic equipment, or where vertical supports are utilized for supporting ancillary equipment such as overhead lights. Since such secondary contacts with the patient are commonly in localized areas, the current density at these areas can be high and hence result in electrosurgical burns at these contact points.

Electrosurgical burns as described hereinabove can be quite severe since the patient is often unconscious during surgery and hence the existence of a condition causing such a burn could go unnoticed for a considerable length of time.

One method for minimizing the burn hazard that has been suggested is to provide an isolated output. It has been found, however, that the safety of such a circuit is limited by RF leakage currents, which depend upon output-to-ground capacitances and the RF waveform. When these factors preclude the use of an isolated output, an internal ground applied to the patient terminal becomes necessary.

While safety circuits have been suggested and/or utilized heretofore in an attempt to prevent such a condition or to at least minimize burns where such a condition comes into existence, it has been found that advantages can be obtained by utilizing a safety circuit with components different from those heretofore suggested and/or utilized. An electrosurgical safety circuit is shown, for example, in U.S. Pat. No. 3,683,923 issued Aug. 15, 1972, to Robert K. Anderson and assigned to the assignee of the present invention.

SUMMARY OF THE INVENTION

This invention provides an improved safety monitoring circuit that is particularly useful in an electrosurgical unit to sense the current flow in the return path and responsive thereto indicating a fault due to improper patient contact with the patient electrode or a disruption in the normal return path. The safety monitoring circuit of this invention is capable of preventing large current flow through an internal ground under a fault condition where such a ground is needed as brought out hereinabove. The described embodiment of the invention includes a current sensor the output from which is coupled to a comparator which provides an output when a predetermined threshold is exceeded with the output from the comparator triggering a timer that energizes, for a predetermined period of time, an alarm and/or disables the RF current flow in the utilization means.

It is, therefore, an object of this invention to provide a new and novel safety monitoring circuit.

It is another object of this invention to provide a new and novel safety monitoring circuit that is useful in an electrosurgical unit to prevent patient burns.

It is still another object of this invention to provide a new and novel safety monitoring circuit that is accurate and quite reliable.

It is another object of this invention to provide a new and novel safety monitoring circuit that actuates an alarm for a predetermined period of time if a ground fault is sensed.

It is still another object of this invention to provide a new and novel safety monitoring circuit for an electrosurgical unit that automatically disrupts, for a predetermined period of time, the application of power to an active electrode in contact with a patient upon sensing of a return fault.

It is yet another object of this invention to provide a new and novel safety monitoring circuit that includes a current sensor, a comparator, and a timer which are utilized in combination to actuate fault indicating means when current sensed in a return path exceeds a predetermined level.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a diagram, partially in pictorial, block and schematic form, illustrating the safety monitoring circuit of this invention incorporated into an electrosurgical unit; and FIG. 2 is an electrical schematic diagram of a portion of the safety monitoring device shown in block form in FIG. 1.

DESCRIPTION OF THE INVENTION

Referring to the drawings, the numeral 7 indicates generally the safety monitoring circuit of this invention and is shown incorporated into an electrosurgical unit 9. Electrosurgical units of the type illustrated are well known and accordingly only those portions of the unit necessary for an understanding of the safety monitoring circuit of this invention are described herein.

As shown in FIG. 1, secondary winding 11 of the output transformer of an RF source (not shown) is connected at the active side through active path, or conductor, 12 to an electrosurgical instrument, or active electrode, 13. As is well known, such an electrosurgical instrument is commonly utilized for either cutting or coagulating (or a combination of both) and is brought into contact with a patient 15 at the point where an operation is to be performed. As also indicated in FIG. 1, the patient is preferably placed into contact with a relatively large patient electrode or plate, 17 which is connected to the return conductor 18, which conductor provides a return path to the patient terminal of secondary winding 11.

As also indicated in FIG. 1, switches 20 and 21, activated by a relay 22, can be provided in the line to disrupt application of RF power from an RF source to the electrosurgical instrument contactable with the patient and with the return path from the patient electrode to such an RF source. A secondary or parallel return path has been indicated in FIG. 1 by means of lead 24 and resistor 25. As brought out hereinabove, such a path could be established in several diverse manners.

As also shown in FIG. 1, current flow through the secondary return path 24 and resistor 25 is returned to secondary winding 11 through current sensor 27 and capacitor 29 connected in series with one another. In the prior art, the secondary return through path 24 and resistor 25 was commonly directly through ground back to secondary winding 11.

Current sensor 27 is preferably an RF thermocouple which is a device that is inherently sensitive to rms current, and is thus desirable for electrosurgical use where threshold current is preferably not dependent upon the mode of operation (i.e., cut, coagulation, or a combination of both).

Capacitor 29 is optional and provides an impedance which has a low value at RF frequencies and a high value at low frequencies so that the 60 Hz line frequency sink capability of the electrosurgical unit will not be dangerous. Capacitor 29 may be, for example, a single capacitor having a high value such that its impedance at the frequencies where RF current will be conducted will be low so that the voltages across the ground line will be sufficiently low to prevent a hazard to the patient. Such a capacitor may be, for example, of a value of 2000 pf.

As also shown in FIG. 1, the output from current sensor 27 is coupled through DC amplifier, or signal conditioning means, 31 to comparator, or interface means, 33. The output from comparator 33 is coupled to triggered timer 35, the output from which is utilized to energize alarm 37 and/or relay 22. The energization of relay 22, of course, causes switches 20 and 21 to be opened and thus terminates the application of RF energy to a patient. The switching arrangement provided by relay 22 and switches 20-21 could, of course, be provided by other arrangements, such as, for example, by supplying a control signal to the RF source circuitry (not shown) to effect a decrease of the output level of the RF source. When utilizing such an arrangement, an output from interface means 33 could be coupled to an RF generator driving transformer winding (not shown) at the RF source to be controlled.

The use of a current sensor placed in series with the ground line allows use of circuitry including a comparator to establish a threshold such that current above a certain value will trigger the alarm and/or disabling circuit, while permitting currents below the threshold level to pass without energizing the alarm and/or disabling circuit. In addition, by providing a variable reference voltage to the comparator, the threshold can, of course, be adjusted as desired. When the sensed current from the current sensor exceeds the comparison reference voltage, an output is provided to timer 35 to energize the alarm 37 and/or disabling circuit. Timer 35 is utilized so that the alarm and/or disabling circuit can be energized for only a predetermined amount of time so that reset action is unnecessary in that the apparatus will automatically reset at the end of the timed period.

FIG. 2 illustrates, in electrical schematic form, DC amplifier 31, comparator 33, triggered timer 35, and alarm 37, along with associated circuitry. While not shown, a shield can be provided for amplifier 31 and comparator 33. As shown, the input from the RF thermocouple (current sensor) 27 is coupled to the positive (+) input (pin 5) of DC amplifier 31 through series connected resistors 39 and 40 with resistor 39 being connected at one side to resistor 41 and at the other side to ground through capacitor 43 with the other side of resistor 40 being connected to ground through capacitor 44.

The other side of thermocouple 27 is connected to the negative (−) input (pin 4) of DC amplifier 31 through series connected resistors 46 and 47 with resistor 46 being connected at one side to resistor 41 and at the other side with ground through capacitor 49, while resistor 47 is connected at the other side with ground through capacitor 50. In addition, pins 4 and 10 of DC amplifier 31 are connected through resistor 51, and pin 11 is connected to a +20 volt power supply through resistor 53 which resistor has capacitor 54 connected with ground at the pin 11 side thereof. Pin 6 of DC amplifier 31 is connected to a −v supply through resistor 56 which resistor has capacitor 57 connected with ground at the pin 6 side thereof.

The output from DC amplifier 31 is coupled from pin 10 through resistor 59 to the negative (−) input side (pin 2) of comparator 33. Comparator 33 has a resistor 60 connected between pins 2 and 6, with pin 3 being connected through resistor 62 to the center tap of potentiometer 63. Potentiometer 63 is connected in series with resistor 65 to define a voltage divider between the +20 volt power supply and ground. The junction of potentiometer 63 and resistor 65 has a by pass capacitor 66 to ground, while the pin 3 side of resistor 62 has a by pass capacitor 67 to ground. Pin 7 of comparator 33 is connected with the +20 volt power supply through resistor 69 and with ground through by pass capacitor 70. Pin 4 of comparator 33 is connected with the −v supply through resistor 72 and with ground through by pass capacitor 73.

The output from comparator 33 is taken from pin 6 and coupled through series connected resistors 75 and 76 to pin 2 of triggered timer 35, with the junction between resistors 75 and 76 having a by pass capacitor 77 to ground. Power is supplied to timer 35 through series connected resistor 79 and Zener diode 80 with resistor 81 being connected to the junction of resistor 79 and pins 4 and 8 of the timer. In addition, capacitor 82 is connected between ground and pins 4 and 8 of the timer, while pin 5 is connected with ground through capacitor 83, and pin 7 is connected with ground through capacitor 84.

The output from triggered timer 35 is taken through resistor 86 to the base of transistor 87, the emitter of which is connected with ground while the collector is connected through resistor 89 to indicator 37, which indicator, in turn, is connected to a +60 volt power supply. The parallel output from timer 35 is taken through resistor 90 and coupled to relay 22.

Particular components which have been utilized in a working embodiment of this invention are as follows, it being realized that the particular components specified are for illustration only and that the invention is not meant to be limited thereto:

DC amplifier 31—LM207
Comparator 33—741
Timer 35—NE555
Zener diode 80—5.6 V
Transistor 87—2N3568
Resistors (ohms): 39, 40, 46 and 47—510 ohms; 41—10 ohms; 51—510K; 53, 56, 69, 72 and 79—51 ohms; 59 and 62—5.6K; 60—5.6M; 65—20K; 75 and 76—1K; 81—1.8M; 86 and 90—2.2K; and 89—100 ohms
Potentiometer 63—0 to 20 Kohms
Capacitors: 29—2000 pf; 43, 44, 49, 50, 54, 57, 67, 70, 73, 77, 82 and 83—0.01 μfd; 66 and 84—1 μfd.

In operation, the safety monitoring circuit of this invention, when used with an electrosurgical unit, senses current flow in the return path and so long as the current flow remains below a predetermined level, as determined by the reference voltage at the comparator 33, the electrosurgical unit operates normally and the circuit continues to monitor current flow without affecting operation of the electrosurgical unit. If the flow exceeds a predetermined maximum level, then comparator 33 provides an output which triggers the triggered timer 35 and the output from the timer 35 energizes an alarm 37 which is shown as a light but could be an audible alarm, if desired. In addition, the output from triggered timer 35 can also be utilized to terminate the application of RF energy to the electrosurgical instrument contactable with a patient. As indicated, this can be accomplished by utilizing a relay 22, for example, to open switches 20 and 21. At the end of the timed period, as determined by timer 35, the alarm 37 is deenergized and the circuit automatically reactivated to apply again RF energy to the electrosurgical instrument. This precludes the necessity of resetting by the operator and, of course, if the fault has not been corrected, the alarm 37 will again be energized and application of power again discontinued if disabling circuitry is utilized. After the fault has been corrected, the automatic reset occurring at the end of the timed period will cause normal operation of the electrosurgical unit to be resumed.

What is claimed is:

1. A radio-frequency electrosurgical device which comprises a radio-frequency generator, a power lead and a return lead, means for coupling the power lead and the return lead to the radio-frequency generator, an active electrosurgical electrode, means for coupling the power lead to the active electrosurgical electrode to power the active electrode, a passive electrode, means for coupling the passive electrode to the return lead, alternate path return means for coupling the return lead to ground at a point between the passive electrode and the radio-frequency generator, and means in the alternate path return means for indicating a predetermined radio-frequency return in the alternate path return means.

2. A device as in claim 1 where said indicating means in the alternate path return means is sensitive to rms current.

3. A device as in claim 1 including frequency sensitive impedance means disposed in series with said indicating means in the alternate path return means having a first value of impedance at 60 Hz and a second value of impedance at a frequency substantially greater than 60 Hz where the second value is less than that of the first value.

4. A device as in claim 3 where said frequency substantially greater than 60 Hz is a radio frequency corresponding to that of the radio-frequency generator.

5. A device as in claim 3 where said frequency sensitive impedance means is a capacitor.

6. A device as in claim 5 where the value of said capacitor is about 2000 pf.

7. A device as in claim 1 including timing means responsive to said indicating means in the alternate return path means for preventing the application of the output of said radio-frequency generator to said active and passive electrodes for a predetermined period of time after the indicating means indicates said predetermined radio-frequency return.

8. A device as in claim 1 where said means for coupling the power and return leads to the radio-frequency generator comprises a transformer.

* * * * *